United States Patent
Thoné

(10) Patent No.: US 11,253,479 B2
(45) Date of Patent: Feb. 22, 2022

(54) HYDROBROMIDE SALT OF AN ANTI-HIV COMPOUND

(71) Applicant: Janssen Sciences Ireland UC, Little Island (IE)

(72) Inventor: Daniel Joseph Christiaan Thoné, Beerse (BE)

(73) Assignee: Janssen Sciences Ireland Unlimited Company, Co Cork (IE)

( * ) Notice: Subject to any disclaimer, the term of this patent is extended or adjusted under 35 U.S.C. 154(b) by 618 days.

(21) Appl. No.: 15/795,873

(22) Filed: Oct. 27, 2017

(65) Prior Publication Data

US 2018/0049986 A1 Feb. 22, 2018

Related U.S. Application Data

(63) Continuation of application No. 12/517,665, filed as application No. PCT/EP2007/063386 on Dec. 6, 2007, now abandoned.

(30) Foreign Application Priority Data

Dec. 6, 2006 (EP) .................... 06125547

(51) Int. Cl.
  *A23K 50/10* (2016.01)
  *A23K 20/158* (2016.01)
  *A61K 9/16* (2006.01)
  *A61K 9/14* (2006.01)

(52) U.S. Cl.
  CPC .......... *A61K 9/1635* (2013.01); *A61K 9/1641* (2013.01); *A61K 9/1652* (2013.01); *A61K 9/145* (2013.01)

(58) Field of Classification Search
  None
  See application file for complete search history.

(56) References Cited

U.S. PATENT DOCUMENTS

2005/0142188 A1  6/2005  Gilis et al.

FOREIGN PATENT DOCUMENTS

| EP | 1225874 B1 | 2/2006 |
| WO | WO 00/27825 A1 | 5/2000 |
| WO | WO 2005/011702 A1 | 2/2005 |

OTHER PUBLICATIONS

Winston et al. ("The clinical pharmacology of antiretrovirals in development." (2006): 447-458).
Scholler et al. (Substantial improvement of oral bioavailability of TMC125 using new tablet formulations in healthy volunteers . . . Poster Exhibition: The 3rd IAS Conference on HIV Pathogenesis and Treatment: Abstract No. TuPe3.1B11 Jul. 24-27, 2005; Rio de Janeiro, Brazil).
Siepmann et al. ("Modeling of drug release from delivery systems based on hydroxypropyl methylcellulose (HPMC)." Advanced drug delivery reviews 48.2 (2001): 139-157).
Reier et al. ("Microcrystalline cellulose in tableting." Journal of Pharmaceutical Sciences 55.5 (1966): 510-514).
International Search Report PCT/EP2007/063386, dated Mar. 12, 2009.
Raoof, A., et al. "The pharmacokinetics of TMC125 in different mouse strains: Impact on Carcinogenicity Testing Strategy". FDA Science—The Critical Path From Concept to Consumer. 11th Annual FDA Science Forum, Apr. 27-28, 2005 (Abstract).
Verbeeck, J., et al. The Pharmacokinetics of TMC125 in different mouse strains: Impact on Carcinogenicity Testing Strategy Abstracts/ Toxicology Letters 158S (2005)—SI-S258.

*Primary Examiner* — Layla Soroush
(74) *Attorney, Agent, or Firm* — Sofia Kopelevich

(57) ABSTRACT

Solid dispersions and dosage forms comprising the hydrobromide salt of a diarylpyrimidine derivative, useful as an anti-HIV agent.

15 Claims, No Drawings

HYDROBROMIDE SALT OF AN ANTI-HIV COMPOUND

CROSS-REFERENCE TO RELATED APPLICATIONS

This application is a continuation of U.S. patent application Ser. No. 12/517,665 filed on Jun. 4, 2009, now pending, which is a 35 U.S.C. § 371 nationalization of PCT Application No. PCT/EP2007/063386, filed on Dec. 6, 2007, which claims priority to European Patent Application No. 06125547.7, filed Dec. 6, 2006, each of which are incorporated herein in its entirety.

This invention concerns the hydrobromide salt of a diarylpyrimidine derivative that is useful as an anti-HIV agent. It further concerns solid dispersions as well as pharmaceutical dosage forms comprising this salt.

The human immunodeficiency virus (HIV) is generally recognized as the agent causing the acquired immunodeficiency syndrome (AIDS), of which two distinct types have been identified, i.e. HIV-1 and HIV-2. Hereinafter, the term HIV is used to generically denote both these types. The spread of HIV has caused and continues to cause serious health problems throughout the world. Consequently, the search for effective pharmaceutical agents to treat HIV infection is of vital importance. AIDS patients are currently treated with a variety of agents such as HIV reverse transcriptase inhibitors (RTIs), HIV protease inhibitors (PIs) and HIV entry inhibitors. One class of anti-HIV pharmaceutical agents comprises the non-nucleoside reverse transcriptase inhibitors (NNRTIs).

WO 00/27825 discloses a series of pyrimidine derivatives that function as NNRTIs. A particularly successful type of NNRTI disclosed in WO 00/27825 is 4-[[4-amino-5-bromo-6-(4-cyano-2,6-dimethylphenyloxy)-2-pyrimidinyl]amino]benzonitrile, also known as etravirine or TMC125, and which is represented by the formula (A):

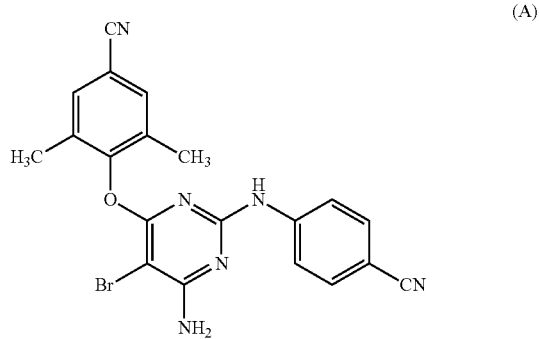 [SMILES: Cc1cc(C#N)cc(C)c1Oc1nc(Nc2ccc(C#N)cc2)nc(N)c1Br]

(A)

The compound of formula (A) has high intrinsic activity not only against wild-type HIV but also against HIV strains harboring resistance-inducing mutations. Consequently, the compound of formula (A) is very useful in the treatment of individuals infected by HIV. Yet its proper functioning is impeded by its very poor solubility in water and concomitant low bioavailability.

One consequence of a pharmaceutical agent having low bioavailability is that the amount (or dose) administered to a patient needs to be higher than it would be if the bioavailability were higher. An increased dose however not only results in an increased risk of side effects and intolerance to the pharmaceutical agent but also leads to an increase in the size and/or the number of dosage forms required.

The number or volume of dosage forms that needs to be administered is commonly referred to as the "pill burden". A high pill burden is undesirable for many reasons, such as the patient having to spend more time taking each dose and the patient having to store and/or transport a large number or volume of pills. A high pill burden also increases the risk that patients will not take their entire dose, thereby failing to comply with the prescribed dosage regimen. As well as reducing the effectiveness of the treatment, this may also lead to the disease-causing organism or virus becoming resistant to the pharmaceutical agent.

The problems associated with a high pill burden are multiplied where a patient must take a combination of a number of different types of pharmaceutical agents. One example of such a group of patients is that being treated for HIV. Anti-HIV treatment generally involves administration of a combination of a number of different pharmaceutical agents. In such cases, therefore, a high pill burden is a particular disadvantage. Having a high pill burden also means that patients infected with HIV may be less able to discreetly take the required doses of pharmaceutical agent(s). This may be a particular problem for those who do not wish their condition to become widely known.

It is known that the degree of crystallinity of a poorly water-soluble pharmaceutical agent is inversely proportional to its bioavailability. As such, the more crystalline the pharmaceutical agent is, the lower its bioavailability. Increased bioavailability may be achieved by providing the pharmaceutical agent in an amorphous form. One way of achieving this is by incorporating the active ingredient into a solid dispersion wherein the active ingredient is dispersed in amorphous form throughout a polymeric matrix, which typically is a water-soluble pharmaceutically acceptable polymeric material. Solid dispersions can be obtained in several ways, e.g. by dissolving the active ingredient and the matrix polymer, optionally in the presence of other ingredients, and allowing the solvent to evaporate. Melt extrusion offers another method to obtain solid dispersions. The spray drying technique offers still another way of obtaining solid dispersions of active ingredients. In this technique a solution of the active ingredient and a polymer, optionally together with other ingredients, is sprayed thereby allowing the solvent to evaporate thus obtaining finely dispersed particles.

As mentioned above, the compound of formula (A) suffers from poor bioavailability thereby impeding its proper functioning. Therefore there is need to improve the bioavailability of this active ingredient so that its beneficial properties can have full play. A higher bioavailability moreover helps to reduce the size and number of dosage forms to be administered and this in turn contributes to an even further reduced pill burden. It now has been found that the hydrobromic acid-addition salt form of the compound of formula (A) has improved bioavailability and is particularly attractive when used in the form of solid dispersions, in particular in the form of solid dispersions prepared by the spray-drying technique.

Thus in one aspect of this invention, there is provided a solid dispersion of a compound of formula (I)

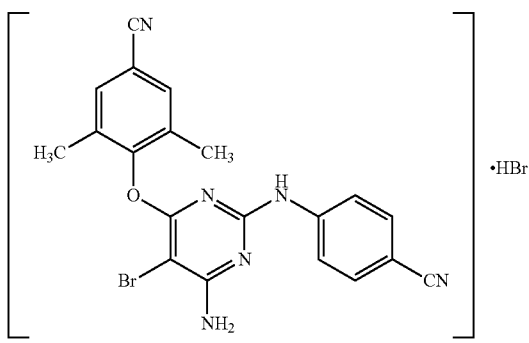

in a water-soluble polymer. In one embodiment, the said solid dispersion is a spray-dried solid dispersion.

In another aspect there is provided the use of a compound of formula (I) for preparing a solid dispersion of the compound of formula (I) in a water-soluble polymer. In one embodiment said use is for preparing a solid dispersion of said compound of formula (I) by spray-drying.

In another aspect there is provided a method of preparing a solid dispersion of the compound of formula (I) in a solid polymeric matrix, said method comprising dispersing the compound of formula (I) into a solid polymeric matrix. In one embodiment said method is by spray-drying.

In a further aspect there is provided a pharmaceutical formulation comprising a solid dispersion of a compound of formula (I) in a solid polymeric matrix, and a carrier. In one embodiment, said formulation comprises a spray-dried solid dispersion of a compound of formula (I).

The compound of formula (I), i.e. 4-[[4-amino-5-bromo-6-(4-cyano-2,6-dimethylphenyloxy)-2-pyrimidinyl]amino] benzonitrile hydrobromide, which is the hydrobromide salt of the compound of formula (A), is deemed novel. Therefore, in a further aspect, the present invention concerns said compound of formula (I). In one embodiment, the compound of formula (I) is in amorphous form. In a further aspect of the invention there are provided pharmaceutical formulations comprising the compound of formula (I) and a carrier. In these formulations, the compound of formula (I) is present in an effective amount, i.e. an amount that is effective to inhibit HIV.

Contrary to a number of other salts of compound (A) that are unstable, the compound of formula (I) is a stable salt. For example the maleate and methane sulfonate salts of compound (A) have been found to be unstable, because of their partial or complete decomposition to compound (A) and the free acid.

The compound of formula (A) may be prepared according to the method described in WO 00/27825. The compound of formula (I) may be prepared by treating the compound of formula (A) with hydrobromic acid.

The compound of formula (I) is useful in the treatment of individuals infected by HIV. It can be used to inhibit HIV and additionally to treat conditions associated with HIV infection. The latter include AIDS as well as secondary conditions associated with HIV infection such as thrombocytopaenia, Kaposi's sarcoma, and infection of the central nervous system characterized by progressive demyelination, resulting in dementia and symptoms such as progressive dysarthria, ataxia, and disorientation. Other conditions associated with HIV infection comprise peripheral neuropathy, progressive generalized lymphadenopathy (PGL), and AIDS-related complex (ARC).

It has been found that the compound of formula (I) has increased bioavailability and that dosage forms comprising the compound of formula (I) advantageously have a lower pill burden.

The compound of formula (I) is preferably highly amorphous, that is, it has a low level of crystallinity. By "amorphous" is meant that the active agent is in a non-crystalline state. This again advantageously increases the bioavailability of the compound of formula (I) thereby decreasing the amount of compound that needs to be administered to a patient resulting in a reduced pill burden.

Preferably, the degree of crystallinity of the pharmaceutical agent in the solid pharmaceutical composition, as characterized by X-ray powder diffraction (XRPD), is about 20% or less, about 15% or less, about 10% or less, about 9% or less, about 8% or less, about 7% or less, about 6% or less, about 5% or less, about 4% or less, about 3% or less, about 2% or less, about 1% or less, about 0.5% or less, or about 0.1% or less.

The compound of formula (I) may be formulated into a dosage form for administration to a patient. Typical dosage forms include dosage forms for administration orally, rectally, vaginally, percutaneously or by parenteral injection. Suitable dosage forms for oral administration include tablets, capsules, powders, pills, suspensions, and solutions. Preferred dosage forms for oral administration are tablets and capsules. Suitable dosage forms for rectal or vaginal administration include gels, suppositories, or pastes.

The compound of formula (I) may be combined with any suitable pharmaceutically acceptable excipient appropriate for the particular dosage form being prepared. For example, for dosage forms for oral administration, suitable excipients include water, glycols, oils, alcohols, starches, sugars, kaolin, diluents, lubricants, binders, and disintegrating agents. Where the dosage form is a solution, polyethylene glycol is preferably used as the vehicle wherein the compound of formula (I) is dissolved. More preferably the polyethylene glycol is PEG 400.

The compound of formula (I) is particularly useful to formulate into a solid dispersion comprising the compound of formula (I), a pharmaceutically acceptable water-soluble polymer, and optionally one or more excipients. Thus formulated, the bioavailability of the compound of formula (I) is improved. Different types of solid dispersions exist. In a first type of solid dispersion the pharmaceutical agent is molecularly dispersed, substantially homogeneously, throughout the polymer. This is generally described as a "solid solution". A second type of solid dispersion is where there are islands of crystalline or semi-crystalline pharmaceutical agent dispersed throughout the polymer. A third type of solid dispersion is where there are islands or clusters of pharmaceutical agent in amorphous form dispersed throughout the polymer.

Spray-drying offers an attractive technique for preparing solid dispersions because it is a continuous process that can be used at large scale. In the spray-drying process, the amount of the compound of formula (I) in the solution introduced to the spray-drying chamber is typically about 10% to about 60%, about 15% to about 50%, about 20% to about 40%, or about 25% to about 35% by weight compared to the total weight of the compound of formula (I), water-soluble polymer and optional excipients. The amount of compound dissolved is determined by its solubility in the solvent(s) chosen.

Polymers suitable for use in the solid dispersions of the compound of formula (I) comprise any that are pharmaceutically acceptable, water-soluble and substantially unreactive towards the pharmaceutical agent. Suitable polymers include cellulosic polymers, such as methyl cellulose, ethyl cellulose, hydroxymethyl cellulose, hydroxy-ethyl cellulose, hydroxypropyl cellulose, hydroxybutyl cellulose, hydroxyethylmethyl cellulose, hydroxypropylmethyl cellulose (HPMC), e.g. HPMC 2910, carboxymethyl cellulose, hydroxypropylmethyl cellulose phthalate (HPMCP), e.g. HP 50, hydroxypropylmethyl cellulose acetate succinate (HPMCAS), cellulose acetate trimellitate (CAT), hydroxypropylcellulose acetate phthalate (HPCAP), hydroxypropylmethyl cellulose acetate phthalate (HPMCAP), methyl cellulose acetate phthalate (MCAP), and mixtures thereof such as a mixture of hydroxypropyl cellulose and ethyl cellulose. Suitable polymers also include polyvinyl pyrrolidone, copolyvidone, which is polyvinyl pyrrolidone copolymerized with vinyl acetate, and aminoalkyl methacrylate copolymers, such as EUDRAGIT E® 100 (Röhm GmbH, Germany). Preferably, the polymer is hydroxypropylmethyl cellulose (HPMC), polyvinyl pyrrolidone or copolyvidone. A particularly preferred hydroxypropylmethyl cellulose is HPMC 2910 5 mPa·s. Particularly preferred polyvinyl pyrrolidones are PVP K12, PVP K30, or PVP K90 and a particularly preferred copolyvidone is PVP-co-VA64.

The amount of water-soluble polymer in the spray dried product may be in the range from about 30% to about 75%, in particular about 40% to about 75%, or about 50% to about 75% or about 60% to about 70%, by weight relative to the total weight of the spray dried product comprising compound (I), i.e. TMC125.HBr, water-soluble polymer and optional excipients. The amount of water-soluble polymer in the feed mixture can be calculated based on these percentages and on the amount of solvent used.

The weight:weight ratio of water-soluble polymer to the compound of formula (I) may be in the range from about 10:1 to about 1:10, in particular from about 10:1 to about 1:1, more in particular from about 5:1 to about 1:1, or from about 4:1 to about 1:1; or from about 3:1 to about 1:1, e.g. a ratio of about 3:1, of about 3.5:1, or of about 3.6:1. The ratio of water-soluble polymer to pharmaceutical agent is believed to affect the degree of crystallinity of the pharmaceutical agent in the resulting solid pharmaceutical composition. However, it is also desirable to reduce the amount of polymer in relation to the pharmaceutical agent in order to maximize the amount of pharmaceutical agent in the resulting pharmaceutical composition.

The solvent used in the spraying process may be any solvent that is inert with respect to the compound of formula (I) and that is able to dissolve the compound of formula (I) and the water-soluble polymer. Mixtures of solvents may be used. Suitable solvents include acetone, tetrahydrofuran (THF), dichloromethane, ethanol (anhydrous or aqueous), methanol, and combinations thereof. Where the polymer is HPMC, the solvent is preferably a mixture of dichloromethane and ethanol, more preferably a mixture of dichloromethane and ethanol, the latter in particular being anhydrous ethanol, in a 9:1 ratio by weight. Where the polymer is polyvinyl pyrrolidone or copolyvidone, the solvent is preferably acetone. The amount of solvent present in the feed mixture will be such that TMC125 and the water-soluble polymer are dissolved and that the feed mixture has sufficient low viscosity for it to be sprayed. In one embodiment the amount of solvent in the feed mixture will be at least 80%, in particular at least 90%, preferably at least 95%, the percentages expressing the weight amount of solvent to the total weight of the feed mixture.

Optionally, the feed mixture may contain further excipients such as to improve the properties of the feed mixture or the resulting solid pharmaceutical composition, for example to improve the handling or processing properties. The addition of excipients obviously results in these being incorporated in the solid dispersion. Regardless of whether or not excipients are added to the feed mixture, these may also be mixed with the resulting solid pharmaceutical composition during formulation into a desired dosage form.

One type of excipient that may be mixed into the feed mixture is microcrystalline cellulose ("MCC"). The microcrystalline cellulose (MCC) that can be used has an average particle size that is selected such that when mixed into the solution of pharmaceutical agent and water-soluble polymer, the resulting feed mixture is able to pass through the atomizing means into the spray-drying chamber without clogging or blocking the atomizer. As such, the size of the MCC is limited by the size of the atomizing means provided on the spray-drying chamber. For example, where the atomizing means is a nozzle, the size of the nozzle bore will affect the size range of the MCC that may be used. The average particle size of the MCC may be in the range of from 5 μm to 50 μm, in particular from 10 μm to 30 μm, e.g. about 20 μm.

Microcrystalline cellulose that can be used comprises the AVICEL™ series of products available from FMC BioPolymer, in particular AVICEL PH 105® (20 μm), AVICEL PH 101® (50 μm), AVICEL PH 301® (50 μm);

the microcrystalline cellulose products available from JRS Pharma, in particular VIVAPUR® 105 (20 μm), VIVAPUR® 101 (50 μm), EMCOCEL® SP 15 (15 μm), EMCOCEL® 50M 105 (50 μm), PROSOLV® SMCC 50 (50 μm);

the microcrystalline cellulose products available from DMV, in particular PHARMACEL®105 (20 μm), PHARMACEL®101 (50 μm);

the microcrystalline cellulose products available from Blanver, in particular TABULOSE (MICROCEL)®101 (50 μm), TABULOSE (MICROCEL)®103 (50 μm);

the microcrystalline cellulose products available from Asahi Kasei Corporation, such as CEOLUS® PH F20JP (20 μm), CEOLUS® PH-101 (50 μm), CEOLUS® PH-301 (50 μm), CEOLUS® KG-802 (50 μm).

A particularly preferred microcrystalline cellulose is AVICEL PH 105® (20 μm).

The amount of MCC in the spray dried product may be in the range from about 5% to about 25%, in particular about 7.5% to about 20%, or about 10% to about 15% or about 10% to about 12.5%, by weight relative to the total weight of the spray dried product comprising TMC125, water-soluble polymer, MCC and optional excipients. The weight ratio of the amounts of MCC to TMC125 in the spray dried product can be calculated based on these percentages and in particular may be in the range of from about 2:1 to about 1:5, in particular from about 1:1 to 1:7, preferably about 1:2. The amount of MCC in the feed mixture can be calculated based on these percentages and on the amount of solvent used. In view of the desirability of keeping the concentration of pharmaceutical agent in the resulting solid pharmaceutical composition as high as possible, the concentration of MCC is preferably kept as low as possible.

A skilled person will be aware of the types of excipients suitable for inclusion in the feed mixture and/or in the resulting pharmaceutical composition. These include surfactants, solubilizers, disintegrants, pigments, flavorings, fillers, lubricants, glidants, preservatives, thickening agents, buffering agents and pH modifiers. Typical surfactants include sodium lauryl sulphate, Cremophor RH 40, Vitamin E TPGS, and polysorbates, such as Tween 20®. Typical pH modifiers are acids, such as citric acid or succinic acid, bases, or buffers.

The solid pharmaceutical composition produced by the process of the invention typically comprises particles having an average effective particle size in the range of from about 10 µm to about 150 µm, or about 15 µm to about 100 µm, particularly about 20 µm to about 80 µm, or 30 µm to about 50 µm, preferably about 40 µm. As used herein, the term average effective particle size has its conventional meaning as known to the person skilled in the art and can be measured by art-known particle size measuring techniques such as, for example, sedimentation field flow fractionation, photon correlation spectroscopy, laser diffraction or disk centrifugation. The average effective particle sizes mentioned herein may be related to weight distributions of the particles. In that instance, by "an average effective particle size of about 150 µm" it is meant that at least 50% of the total weight of the particles is composed of particles having a particle size of less than the effective average of 150 µm, and the same applies to the other effective particle sizes mentioned. In a similar manner, the average effective particle sizes may be related to volume distributions of the particles but usually this will result in the same or about the same value for the average effective particle size.

The so-called "span" of the spray-dried particles may be lower than about 3, in particular lower than about 2.5, e.g. the span is about 2. Usually the span will not be lower than about 1. As used herein the term "span" is defined by the formula $(D_{90}-D_{10})/D_{50}$ wherein $D_{90}$ is the particle diameter corresponding to the diameter of particles that make up 90% of the total weight of all particles of equal or smaller diameter and wherein $D_{50}$ and $D_{10}$ are the diameters for 50 respectively 10% of the total weight of all particles.

The spray-dried particles may be formulated into a pharmaceutical formulation. The latter comprises the spray-dried particles and a carrier, which may comprise one or more pharmaceutically acceptable ingredients such as, for example, a lubricant, a binder, thickener, and the like ingredients. Where the formulation is a suspension or a paste, the spray-dried particles may be added to a suitable liquid, such as water.

The pharmaceutical formulations in turn may be converted into an appropriate dosage form. Typical dosage forms include dosage forms for oral administration, such as tablets, capsules, suspensions and pastilles, and dosage forms for rectal or vaginal administration, such as gels, suppositories or pastes. The spray-dried particles may be subjected to further processing steps depending on the nature of the final dosage form. For example, the pharmaceutical composition may be subjected to a post-drying process, or may undergo tabletting or encapsulating processes. Depending on whether the dosage form comprising the spray-dried particles is intended for immediate release or controlled release, further processing steps may be required, such as the incorporation of a disintegrant for immediate release products or the coating of the powder with an enteric layer for controlled release products. Suitable disintegrants include microcrystalline cellulose, starch, sodium starch glycolate, crosslinked carboxy-methylcellulose sodium, and crosslinked PVP.

The effective daily amount of the compound of formula (I) is from about 1 mg/kg to about 20 mg/kg body weight, or from about 2 mg/kg to about 10 mg/kg body weight, or from about 5 mg/kg to about 8 mg/kg body weight, or from about 5 mg/kg to about 6 mg/kg body weight. The effective daily amounts per patient can be obtained by multiplying the before-mentioned amounts by 70 or by the actual weight of the patient. A person skilled in the art will be able to determine the exact dose and frequency of administration required, which will depend on a number of factors, such as the severity of the condition being treated, the age and weight of the individual being treated and whether that individual is taking any other medication. The effective daily amount of the compound of formula (I) may be administered as a single dose or as two, three, four or more sub-doses at appropriate intervals throughout the day. The dose or sub-doses of the compound of formula (I) may be formulated as unit dosage forms containing a specified amount of the compound, typically from about 10 to about 1000 mg, from about 50 to about 800 mg, from about 100 to about 500 mg, from about 100 mg to about 300 mg, e.g. about 200 mg or about 240 mg of the compound of formula (I).

As used herein the term "about" has its usual meaning as understood by the person skilled in the relevant art. The term "about" may alternatively be interpreted as meaning that the numerical value mentioned in connection with the term "about" can deviate with +/−10%, or with +/−5%, or with +/−1%. All documents cited herein are incorporated by reference in their entirety. Specific embodiments of the present invention are now described, by way of example only, and should not be construed as limiting the invention thereto.

EXAMPLE 1—PREPARATION OF SALTS OF THE COMPOUND OF FORMULA (A)

The compound of formula (A), that is, 4-[[4-amino-5-bromo-6-(4-cyano-2,6-dimethylphenyloxy)-2-pyrimidinyl]amino]benzonitrile, was dissolved in dichloromethane and aqueous hydrobromic acid was added. The mixture was evaporated to dry yielding the hydrobromide salt of (A), i.e. the compound of formula (I). Other addition salts of the compound of formula (A) can be obtained similarly and are shown in the following Table 1.

| Acid | Salt of compound of formula (I) obtained |
|---|---|
| Hydrobromic acid | Hydrobromide (i.e. compound of formula (I)) |
| Hydrochloric acid | Hydrochloride |
| Maleic acid | Maleate |
| Methanesulfonic acid | Methanesulfonate |
| Fumaric acid | Fumarate |
| Sulfuric acid | Sulfate |

Capsules were filled with the various salts of the compound of formula (I) in the amounts shown in the following Table 2.

| Salt of compound (I) | Amount of salt per capsule in mg |
|---|---|
| Hydrobromide | 118.6 |
| Hydrochloride | 108.4 |
| Maleate | 63.3 |
| Methane sulfonate | 122.1 |
| Fumarate | 63.3 |
| Sulfate | 122.5 |

EXAMPLE 2—IN-VIVO STUDY OF BIOAVAILABILITY IN DOGS OF THE COMPOUND OF FORMULA (I) COMPARED WITH SALTS OF THE COMPOUND OF FORMULA (I)

Four male dogs were used per tested formulation. The animals were randomized over the test groups by a computer-generated random algorithm according to body weight, with all animals within ±20% of the sex mean. A health inspection was performed prior to commencement of treatment to ensure that the animals were in a good state of health. The dogs were subjected to an acclimatization period of at least 5 days before the start of treatment under laboratory conditions. A controlled environment was maintained in the room. The animals were dosed once orally with the formulations of example 1, and blood was collected from all animals under light ether anaesthesia at regular intervals for a period of 12, 24 or 48 hours after dosing.

The mean pharmacokinetic parameters relating to the mean plasma concentration with time of each test formulation are shown in Table 3. The standard deviation, where calculated, is shown between brackets. Analysis of the peak plasma concentration ($C_{max}$) and bioavailability in terms of area under the curve ($AUC_{0-last}$) shows that the hydrobromide salt of compound (I), that is the compound of formula (I) has advantageously improved bioavailability in dogs compared with other salts of compound (I). $t_{max}$ is the time taken to reach the peak plasma concentration. $t_{last}$ is the last time at which the peak plasma concentration was determined.

methanol/dichloromethane. HPMC 2910 5 mPa·s was dissolved in methanol/dichloro-methane 50/50 v/v % in a second beaker. The concentration of HPMC 2910 5 mPa·s in the solution was 6.5 g per 100 ml methanol/dichloromethane.

The two solutions were subsequently mixed and then spray-dried using the following spray-drying operating conditions:

Inlet air temperature: 80° C.
Outlet air temperature: 40-55° C.
Flow rate of the solution: 12 ml/min
Air pressure: 1 bar After spray-drying, the spray dried powder was dried under reduced pressure at 40° C. for 5 days. The resulting formulation was filled into Swedish-orange capsules.

An in-vivo dog study of the bioavailability of capsules comprising formulation G was carried out as described in Example 2. The mean pharmacokinetic parameters are shown in Table 6. The standard deviation, where calculated, is shown between brackets.

| Parameter | Formulation G |
|---|---|
| $t_{max}$ (h) | 1.0 (1.0-2.0) |
| $t_{last}$ (h) | 48 (0) |
| $AUC_{0-last}$ (ng · h/ml) (without dose normalization) | 13752 (2378) |
| $C_{max}$ (ng/ml) (without dose normalization) | 1263 (165.6) |
| $AUC_{0-last}$ (ng · h/ml) (dose normalized to 1 mg/kg) | 1179 (293.7) |
| $C_{max}$ (ng/ml) (dose normalized to 1 mg/kg) | 107.0 (15.38) |

| Parameter | HBr salt | HCl salt | Maleate salt | Methane-sulfonate salt | Fumarate salt | Sulfate salt |
|---|---|---|---|---|---|---|
| $t_{max}$ (h) | 4.5 (2.1) | 1.5 (0.7) | 2.0 (—) | 1.5 (0.7) | 2.0 (—) | 2.0 (0) |
| $t_{last}$ (h) | 48 (0) | 48 (0) | 24 (—) | 48 (0) | 12 (—) | 48 (0) |
| $AUC_{0-last}$ (ng · h/ml) (without dose normalization) | 5855 (1456) | 1875 (158.7) | 446.5 (—) | 3753 (803.3) | 102.7 (—) | 3143 (794.3) |
| $C_{max}$ (ng/ml) (without dose normalization) | 365.5 (212.8) | 222.0 (86.27) | 52.00 (—) | 409.0 (57.98) | 15.2 (—) | 294.0 (29.70) |
| $AUC_{0-last}$ (ng · h/ml) (dose normalized to 1 mg/kg) | 516.1 (83.02) | 168.2 (29.43) | 77.70 (—) | 318.8 (35.56) | 20.67 (—) | 279.9 (49.45) |
| $C_{max}$ (ng/ml) (dose normalized to 1 mg/kg) | 31.73 (16.05) | 20.19 (9.513) | 9.048 (—) | 34.87 (1.337) | 3.058 (—) | 26.34 (0.6133) |

EXAMPLE 3—SPRAY-DRIED FORMULATION COMPRISING THE COMPOUND OF FORMULA (I)

| | Formulation G |
|---|---|
| Compound of formula (I) | 59.3 mg |
| HPMC 5 m Pa · s | 177.9 mg |

To prepare formulation G, the compound of formula (I) was dissolved in a first beaker in methanol/dichloromethane 50/50 v/v % at a concentration of 6.5 g per 750 ml of

EXAMPLE 5—IN-VIVO STUDY OF BIOAVAILABILITY IN HUMANS OF THE COMPOUND OF FORMULA (I) FORMULATION L

To prepare formulation L, 118.6 mg of the compound of formula (I) was dissolved in a first beaker in methanol/dichloromethane 50/50 v/v % at a concentration of 6.5 g per 750 ml of methanol/dichloromethane In a second beaker, 234.8 mg HPMC 2910 5 mPa·s was dissolved in methanol/dichloromethane 50/50 v/v %. The concentration of HPMC 2910 5 mPa·s in the solution was 6.5 g per 100 ml methanol/ dichloromethane. The two solutions were subsequently mixed and then sprayed onto 121 mg of HMPC 5 mPa·s. The resulting powder was filled into Swedish-orange capsules. One capsule of formulation L contained 118.6 mg of the compound of formula (I), which is equivalent to 100 mg of compound (A).

A randomized human bioequivalence trial was carried out to monitor bioavailability in humans of formulation L.

For formulation L, nine subjects were given 800 mg of formulation L twice daily for 13 days, with a single dose on day 14. A 12 h pharmacokinetic profile was determined on day 1 and on day 14. Pre-dose concentrations were determined every other day. The results are listed in the following Table.

| Scheduled time | Plasma conc. of TMC125 (ng/ml) Mean ± SD |
|---|---|
| Day 1 | |
| 0 h | Not quantifiable |
| 1 h | 35.3 ± 33.1 |
| 2 h | 638 ± 451 |
| 3 h | 1220 ± 750 |
| 4 h | 136 ± 681 |
| 6 h | 1020 ± 395 |
| 8 h | 680 ± 285 |
| 10 h | 476 ± 182 |
| 12 h | 392 ± 166 |
| Day 3 | |
| 0 h | 1230 ± 341 |
| Day 5 | |
| 0 h | 1630 ± 513 |
| Day 7 | |
| 0 h | 1830 ± 769 |
| Day 9 | |
| 0 h | 1830 ± 720 |
| Day 11 | |
| 0 h | 1940 ± 758 |
| Day 13 | |
| 0 h | 1870 ± 740 |
| Day 14 | |
| 0 h | 1660 ± 578 |

For formulation L, pre-dose levels reached steady-state between 3 to 5 days. Good bioavailability was observed.

The invention claimed is:

1. A solid dispersion comprising a compound of formula (I):

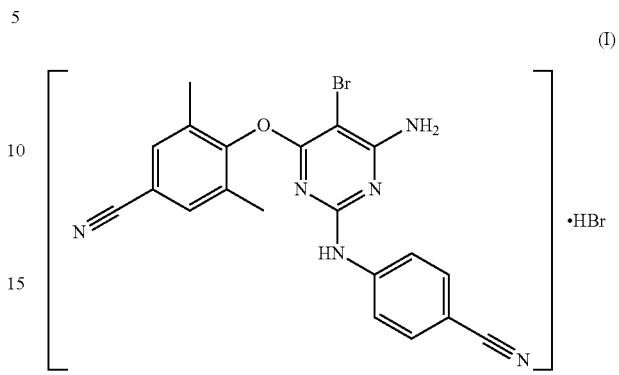

in a water-soluble polymer selected from hydroxypropylmethyl cellulose 2910 5 mPa·s and vitamin E TGPS, wherein the weight:weight ratio of the water-soluble polymer to the compound of formula (I) is about 10:1 or about 9:1.

2. The solid dispersion according to claim 1, wherein the weight:weight ratio of the water-soluble polymer to the compound of formula (I) is about 9:1.

3. A dosage form comprising the solid dispersion of claim 1.

4. The dosage form of claim 3 wherein the dosage form is selected from a tablet and a capsule.

5. The solid dispersion according to claim 1 obtainable by spray-drying.

6. The solid dispersion according to claim 5, further containing microcrystalline cellulose.

7. The solid dispersion according to claim 1, wherein the water-soluble polymer is hydroxypropylmethyl cellulose 2910 5 mPa·s.

8. The solid dispersion according to claim 1, wherein the water-soluble polymer is vitamin E TGPS.

9. The solid dispersion according to claim 7, wherein the weight:weight ratio of the water-soluble polymer to the compound of formula (I) is about 9:1.

10. The solid dispersion according to claim 8, wherein the weight:weight ratio of the water-soluble polymer to the compound of formula (I) is about 9:1.

11. The dosage form of claim 3, wherein the water-soluble polymer is hydroxypropylmethyl cellulose 2910 5 mPa·s.

12. The dosage form of claim 3, wherein the water-soluble polymer is vitamin E TGPS.

13. The dosage form of claim 3, wherein the weight:weight ratio of the water-soluble polymer to the compound of formula (I) is about 9:1.

14. The dosage form of claim 11, wherein the weight:weight ratio of the water-soluble polymer to the compound of formula (I) is about 9:1.

15. The dosage form of claim 12, wherein the weight:weight ratio of the water-soluble polymer to the compound of formula (I) is about 9:1.

* * * * *